(12) United States Patent
Igarashi et al.

(10) Patent No.: US 9,486,127 B2
(45) Date of Patent: Nov. 8, 2016

(54) CAPSULE TYPE MEDICAL DEVICE

(71) Applicant: OLYMPUS CORPORATION, Tokyo (JP)

(72) Inventors: Takatoshi Igarashi, Ina (JP); Noriyuki Fujimori, Suwa (JP); Yukiharu Makino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/192,148

(22) Filed: Feb. 27, 2014

(65) Prior Publication Data

US 2014/0179999 A1  Jun. 26, 2014

Related U.S. Application Data

(63) Continuation of application No. PCT/JP2012/062471, filed on May 16, 2012.

(30) Foreign Application Priority Data

Aug. 31, 2011 (JP) ................ 2011-189703

(51) Int. Cl.
*A61B 1/06* (2006.01)
*A61B 1/04* (2006.01)
*A61B 1/00* (2006.01)

(52) U.S. Cl.
CPC ........... *A61B 1/041* (2013.01); *A61B 1/00016* (2013.01); *A61B 1/00032* (2013.01); *A61B 1/0661* (2013.01)

(58) Field of Classification Search
CPC .. A61B 1/041; A61B 1/00016; A61B 5/073; A61B 5/0031; A61B 5/07; H05K 1/189; H05K 1/148; H05K 1/147

USPC ......... 600/109, 160, 101, 130, 302
See application file for complete search history.

(56) References Cited

U.S. PATENT DOCUMENTS

| | | | |
|---|---|---|---|
| 7,623,904 B2* | 11/2009 | Uchiyama et al. | 600/424 |
| 7,637,865 B2* | 12/2009 | Iddan et al. | 600/130 |
| 7,643,865 B2* | 1/2010 | Iddan et al. | 600/424 |
| 7,775,971 B2* | 8/2010 | Fujimori et al. | 600/110 |
| 7,801,584 B2* | 9/2010 | Iddan et al. | 600/407 |

(Continued)

FOREIGN PATENT DOCUMENTS

| | | |
|---|---|---|
| EP | 1 681 010 A1 | 7/2006 |
| EP | 1 769 720 A1 | 4/2007 |

(Continued)

OTHER PUBLICATIONS

International Search Report dated Jun. 12, 2012 issued in PCT/JP2012/062471.

(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

A capsule endoscope includes a capsule type housing and a circuit board on which a plurality of board sections are arranged in a row, the circuit board being housed inside the housing in a bent state. Connection electrodes for electronic component mounting are not formed on a second principal plane of the circuit board.

10 Claims, 8 Drawing Sheets

(56) References Cited

U.S. PATENT DOCUMENTS

| | | | |
|---|---|---|---|
| 7,801,586 B2* | 9/2010 | Muratayev et al. | 600/407 |
| 7,833,151 B2* | 11/2010 | Khait et al. | 600/109 |
| 7,864,007 B2* | 1/2011 | Fujimori et al. | 335/151 |
| 7,892,164 B2* | 2/2011 | Segawa et al. | 600/109 |
| 7,946,983 B2* | 5/2011 | Fujimori et al. | 600/302 |
| 7,998,059 B2* | 8/2011 | Fujimori | 600/109 |
| 7,998,065 B2* | 8/2011 | Avni | 600/130 |
| 8,348,835 B2* | 1/2013 | Fujimori | 600/160 |
| 8,460,174 B2* | 6/2013 | Segawa et al. | 600/101 |
| 2004/0027459 A1* | 2/2004 | Segawa et al. | 348/207.99 |
| 2004/0171914 A1* | 9/2004 | Avni | 600/160 |
| 2005/0064815 A1* | 3/2005 | Kanazawa | 455/41.1 |
| 2005/0085696 A1* | 4/2005 | Uchiyama et al. | 600/160 |
| 2005/0154294 A1 | 7/2005 | Uchiyama et al. | |
| 2005/0171398 A1* | 8/2005 | Khait et al. | 600/102 |
| 2006/0004257 A1* | 1/2006 | Gilad et al. | 600/160 |
| 2006/0004276 A1* | 1/2006 | Iddan et al. | 600/407 |
| 2006/0015013 A1* | 1/2006 | Gilad et al. | 600/160 |
| 2006/0100496 A1* | 5/2006 | Avron | 600/407 |
| 2006/0104057 A1* | 5/2006 | Avron et al. | 362/227 |
| 2006/0149132 A1* | 7/2006 | Iddan | 600/160 |
| 2006/0224040 A1* | 10/2006 | Khait et al. | 600/102 |
| 2006/0241422 A1* | 10/2006 | Muratayev et al. | 600/435 |
| 2006/0249737 A1* | 11/2006 | Fujimori | 257/79 |
| 2006/0252986 A1* | 11/2006 | Akagi et al. | 600/101 |
| 2006/0258901 A1* | 11/2006 | Fujimori et al. | 600/101 |
| 2006/0264083 A1* | 11/2006 | Fujimori | 439/266 |
| 2006/0264703 A1* | 11/2006 | Fujimori | 600/101 |
| 2006/0264704 A1* | 11/2006 | Fujimori et al. | 600/101 |
| 2006/0264709 A1* | 11/2006 | Fujimori | A61B 1/00029 600/130 |
| 2007/0118012 A1* | 5/2007 | Gilad | 600/109 |
| 2007/0171012 A1* | 7/2007 | Fujimori et al. | 335/151 |
| 2007/0219435 A1* | 9/2007 | Segawa et al. | 600/302 |
| 2008/0021270 A1* | 1/2008 | Suzushima et al. | 600/109 |
| 2008/0021281 A1* | 1/2008 | Fujimori | 600/160 |
| 2008/0033257 A1* | 2/2008 | Yokoi et al. | 600/300 |
| 2008/0039694 A1* | 2/2008 | Fujimori | 600/177 |
| 2008/0058601 A1* | 3/2008 | Fujimori | 600/167 |
| 2008/0068453 A1* | 3/2008 | Mori et al. | 348/65 |
| 2008/0167528 A1* | 7/2008 | Segawa et al. | 600/160 |
| 2008/0183041 A1* | 7/2008 | Fujimori et al. | 600/118 |
| 2008/0281160 A1* | 11/2008 | Segawa | 600/160 |
| 2009/0018398 A1* | 1/2009 | Segawa et al. | 600/178 |
| 2009/0062605 A1* | 3/2009 | Orihara et al. | 600/109 |
| 2009/0105532 A1* | 4/2009 | Gilad | 600/101 |
| 2009/0112058 A1* | 4/2009 | Kagawa | 600/103 |
| 2009/0171146 A1* | 7/2009 | Fujita | 600/102 |
| 2009/0281380 A1* | 11/2009 | Miller et al. | 600/109 |
| 2009/0281401 A1* | 11/2009 | Takenaka et al. | 600/302 |
| 2009/0292167 A1* | 11/2009 | Kimoto | 600/109 |
| 2009/0295386 A1* | 12/2009 | Sato et al. | 324/309 |
| 2009/0299144 A1* | 12/2009 | Shigemori et al. | 600/160 |
| 2010/0016667 A1* | 1/2010 | Segawa | A61B 1/00105 600/118 |
| 2010/0016670 A1* | 1/2010 | Segawa et al. | 600/165 |
| 2010/0016672 A1* | 1/2010 | Segawa et al. | 600/173 |
| 2010/0076258 A1* | 3/2010 | Segawa et al. | 600/101 |
| 2010/0174141 A1* | 7/2010 | Gilad et al. | 600/118 |
| 2010/0326703 A1* | 12/2010 | Gilad | A61B 1/041 174/254 |
| 2011/0306855 A1* | 12/2011 | Rabinovitz et al. | 600/310 |

FOREIGN PATENT DOCUMENTS

| | | |
|---|---|---|
| EP | 2 130 480 A1 | 12/2009 |
| JP | 2005-080933 A | 3/2005 |
| JP | 2005-125010 A | 5/2005 |
| JP | 2005-204802 A | 8/2005 |
| JP | 2006-020852 A | 1/2006 |
| JP | 2006-247081 A | 9/2006 |
| JP | 2006-280940 A | 10/2006 |
| JP | 2007-313340 A | 12/2007 |
| JP | 2008-246148 A | 10/2008 |
| WO | WO 2005039400 A1 | 5/2005 |
| WO | WO 2006006452 A1 | 1/2006 |
| WO | WO 2008123464 A1 | 10/2008 |
| WO | WO 2010/150243 A1 | 12/2010 |

OTHER PUBLICATIONS

Extended Supplementary European Search Report dated May 15, 2015 from related European Application No. 12 82 8480.9.

* cited by examiner

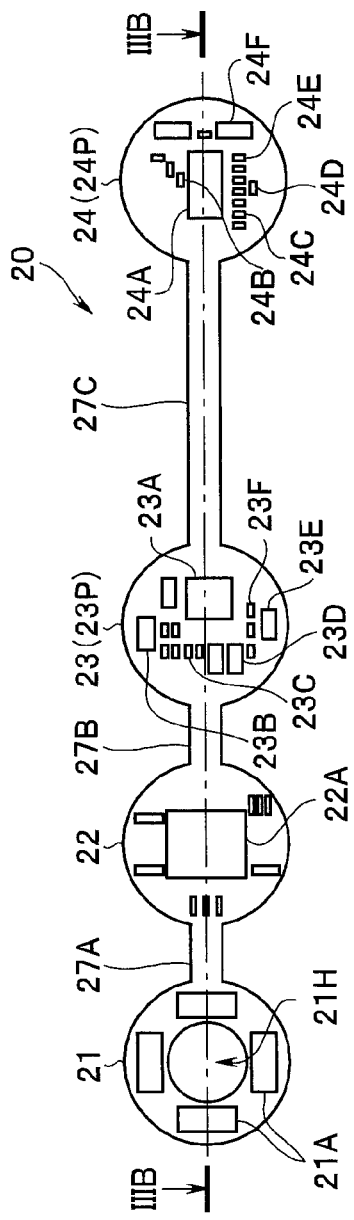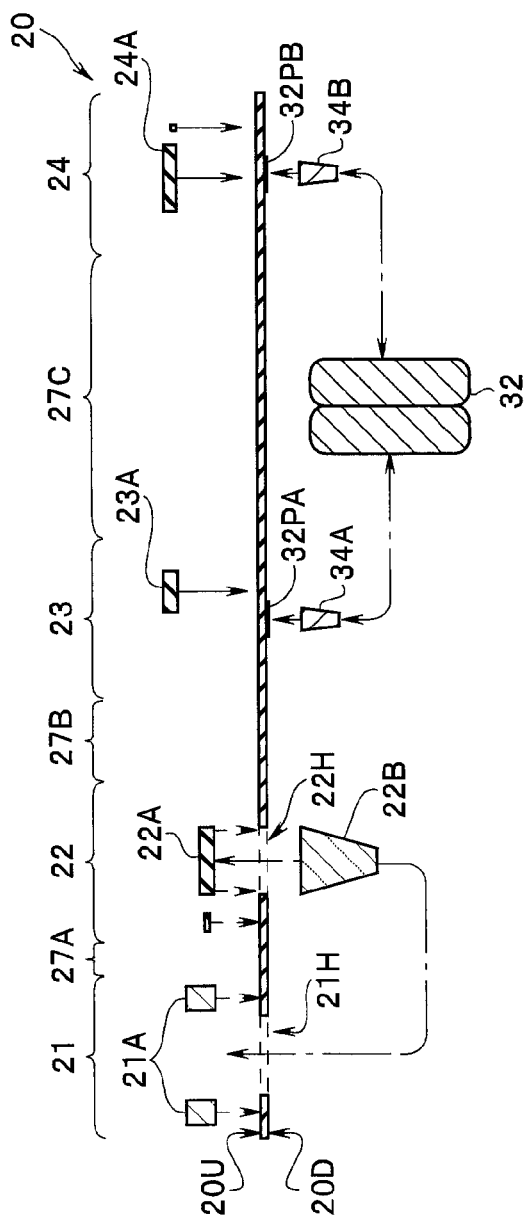
FIG.3A
FIG.3B

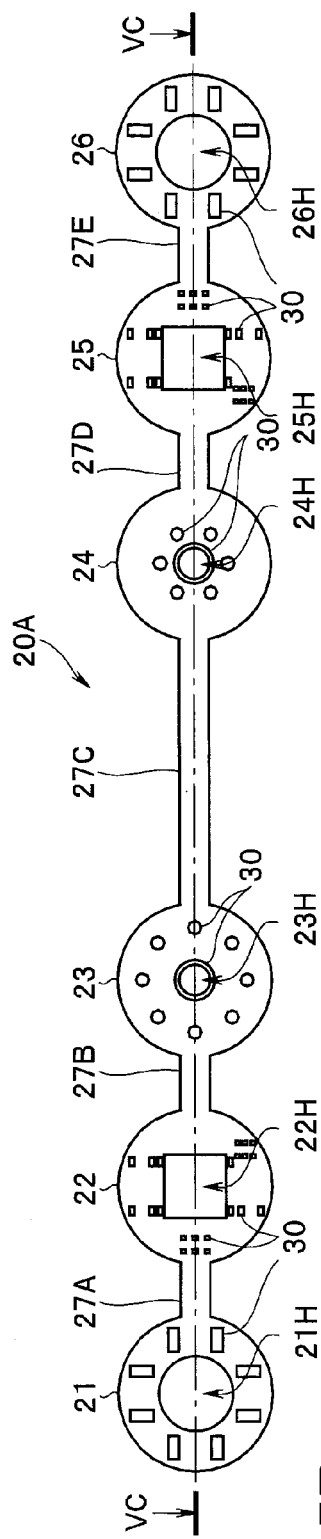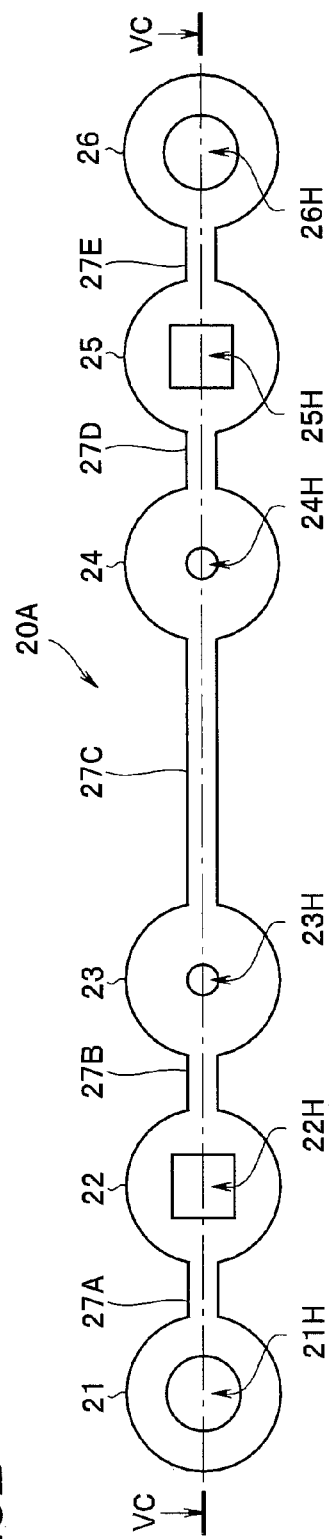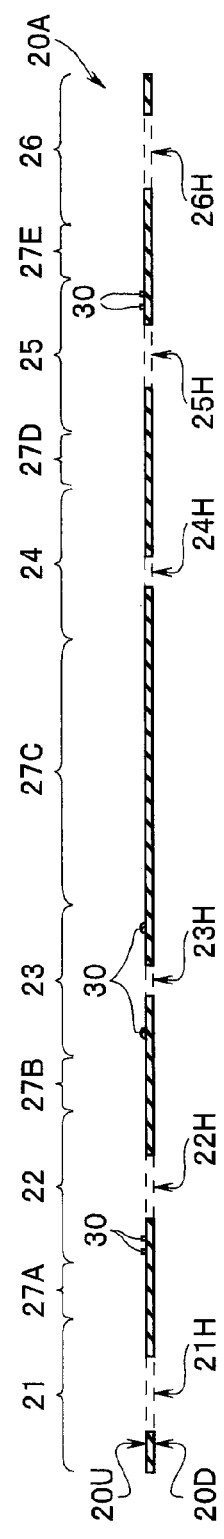
FIG.5A
FIG.5B
FIG.5C

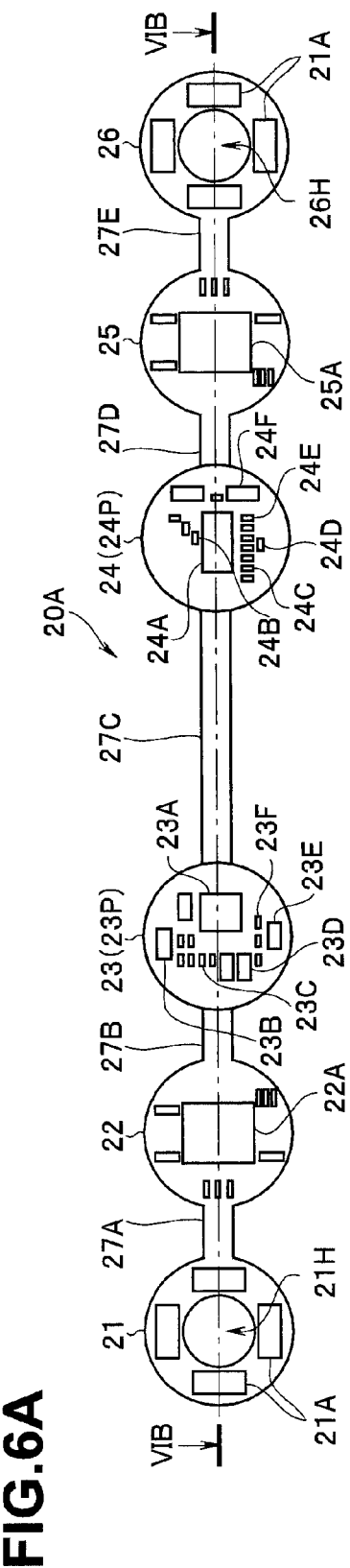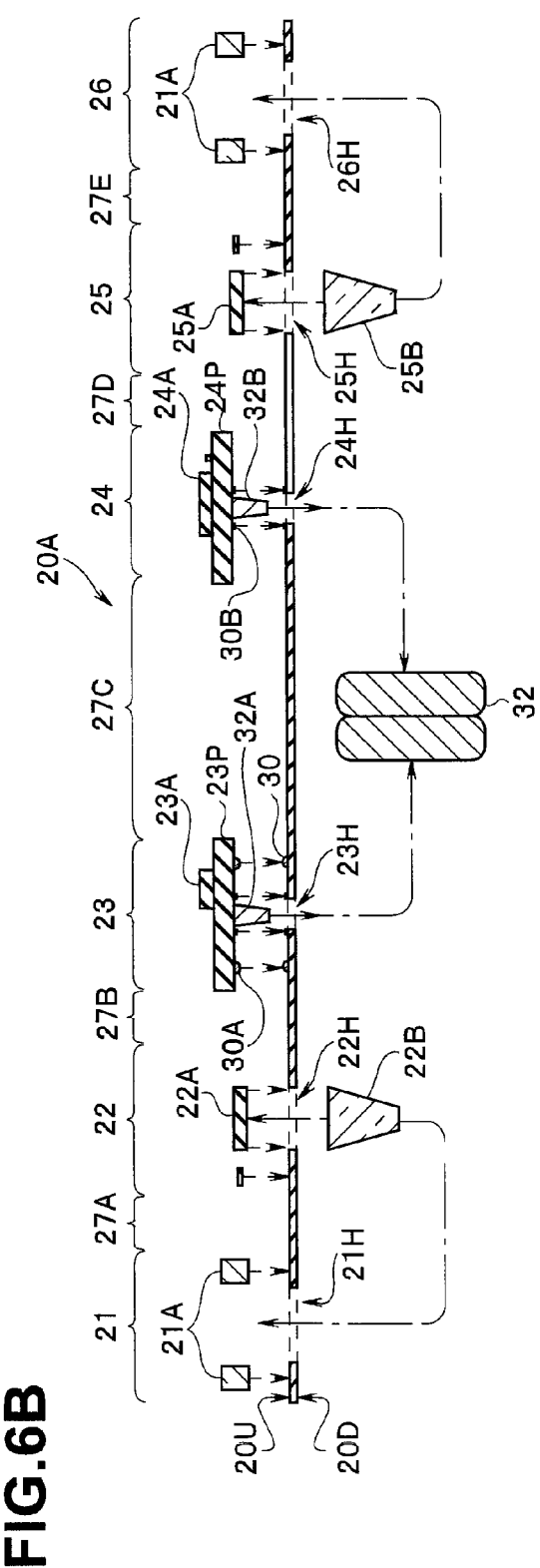
FIG.6A
FIG.6B

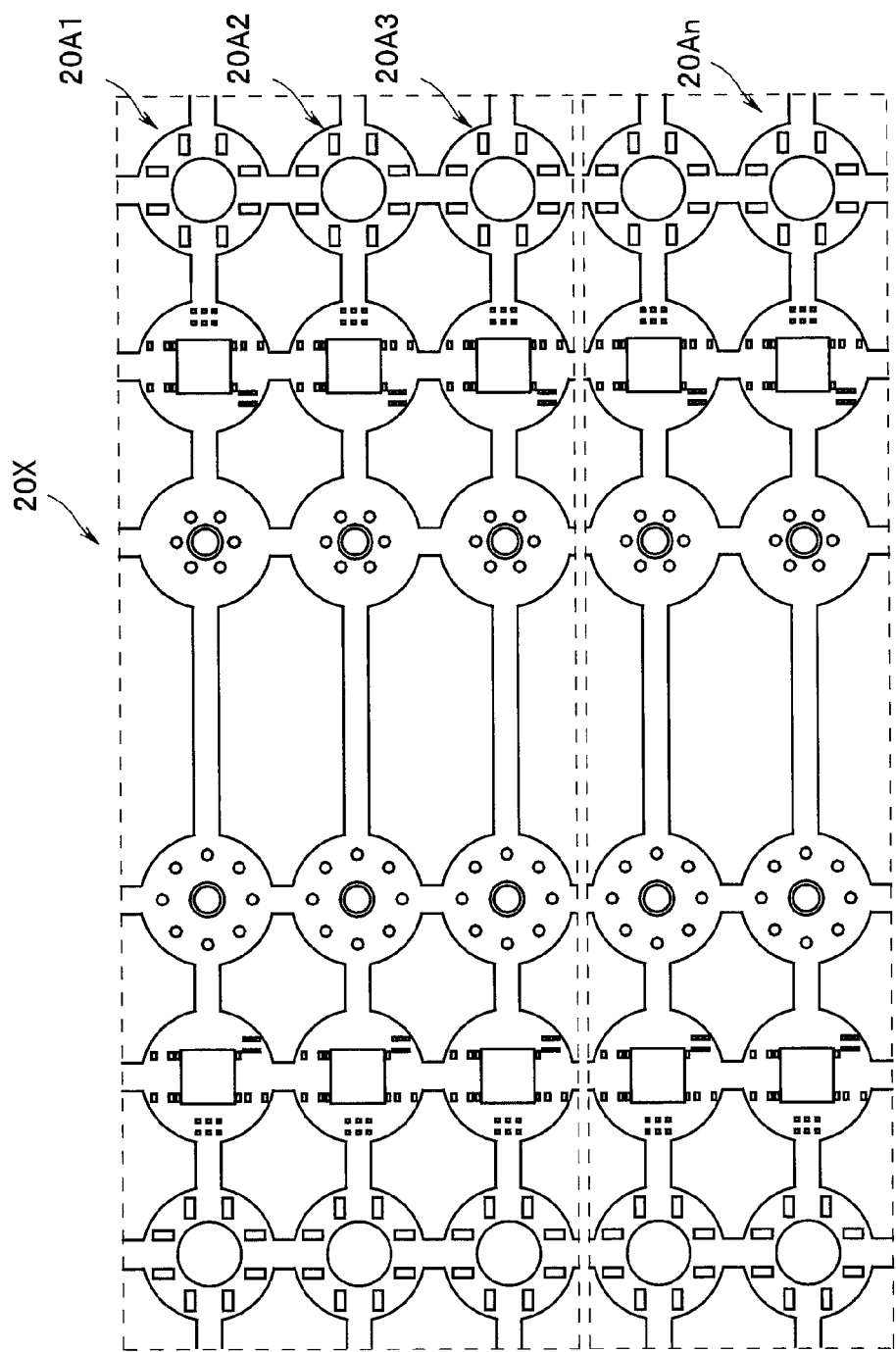

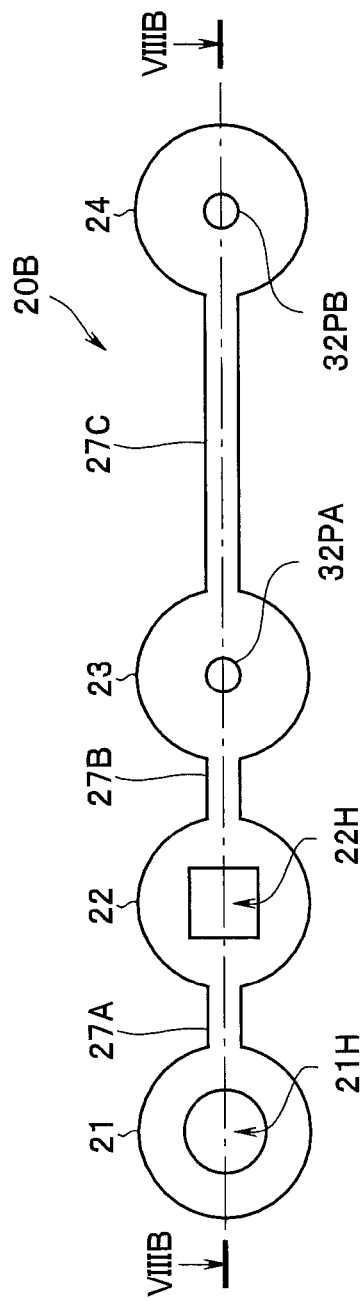
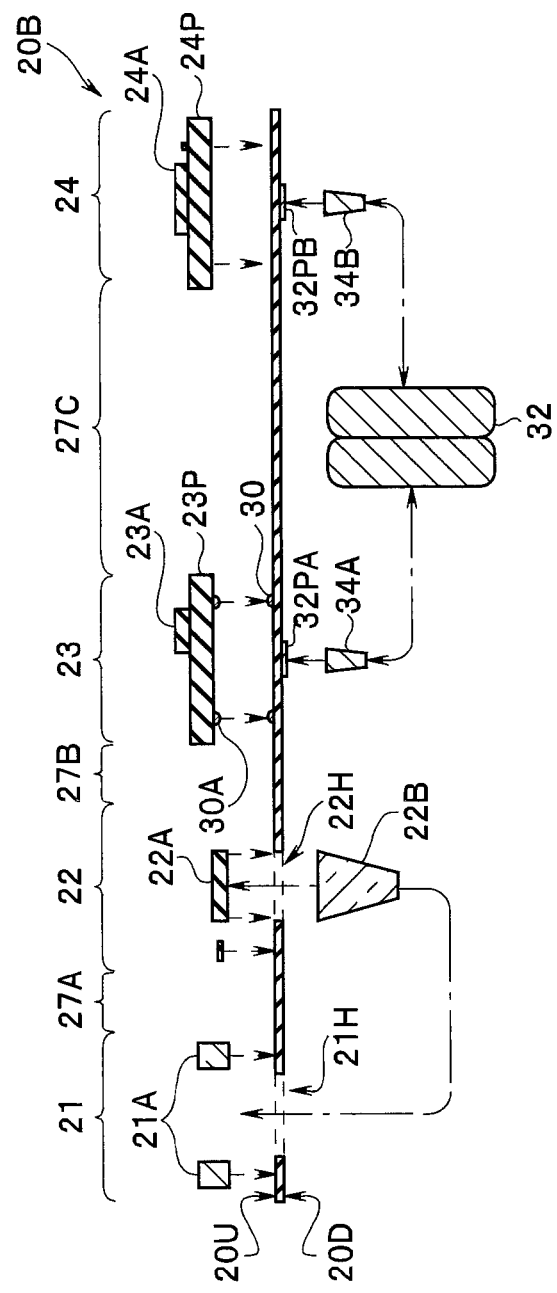
FIG.8A
FIG.8B

CAPSULE TYPE MEDICAL DEVICE

CROSS REFERENCE TO RELATED APPLICATION

This application is a continuation application of PCT/JP2012/062471 filed on May 16, 2012 and claims benefit of Japanese Application No. 2011-189703 filed in Japan on Aug. 31, 2011, the entire contents of which are incorporated herein by this reference.

BACKGROUND OF INVENTION

1. Field of the Invention

Embodiments of the present invention relate to a capsule type medical device introduced into a body.

2. Description of the Related Art

In recent years, a capsule endoscope including an image pickup function and a radio transmission function has emerged in the market. After being swallowed by an examinee, the capsule endoscope moves through digestive tracts such as a stomach and a small intestine following a peristaltic movement and picks up images of insides of organs using the image pickup function until the capsule endoscope is naturally discharged.

Images picked up by the capsule endoscope while the capsule endoscope moves in the digestive tracts are transmitted to an external device provided outside the examinee as an image signal by the radio transmission function and stored in a memory of the external device. After swallowing the capsule endoscope, the examinee can freely act by carrying the external device including a radio reception function and a memory function. After observation by the capsule endoscope, the images stored in the memory of the external device are displayed on a display or the like and diagnosis or the like is performed.

Japanese Patent Application Laid-Open Publication No. 2005-204802 discloses a capsule endoscope in which a rigid flexible wiring board, on which a plurality of substantially circular rigid board sections are joined via a flexible substrate section, is housed in a housing. Various electronic components are mounted on both surfaces of the rigid flexible wiring board.

SUMMARY OF THE INVENTION

According to an aspect of the present invention, there is provided a capsule type medical device including: a capsule type housing and a circuit board including a first principal plane and a second principal plane, the circuit board having a plurality of board sections in a row arranged thereon, and a connection electrode for electronic component mounting is formed on the first principal plane, and the connection electrode is not formed on the second principal plane.

BRIEF DESCRIPTION OF THE DRAWINGS

FIG. 3A is a top view for explaining component mounting on the circuit board of the capsule endoscope in the first embodiment;

FIG. 3B is an exploded sectional view for explaining the component mounting on the circuit board of the capsule endoscope in the first embodiment;

FIG. 5A is a top view for explaining a circuit board before mounting of the capsule endoscope in the second embodiment;

FIG. 5B is a bottom view for explaining the circuit board before mounting of the capsule endoscope in the second embodiment;

FIG. 5C is a sectional view taken along line VC-VC of FIG. 5A and FIG. 5B for explaining the circuit board before mounting of the capsule endoscope in the second embodiment;

FIG. 6A is a top view for explaining component mounting on the circuit board of the capsule endoscope in the second embodiment;

FIG. 6B is an exploded sectional view taken along line VIB-VIB of FIG. 6A for explaining the component mounting on the circuit board of the capsule endoscope in the second embodiment;

FIG. 7 is a top view for explaining a manufacturing method for the circuit board of the capsule endoscope in the second embodiment;

FIG. 8A is a bottom view for explaining a circuit board before mounting of a capsule endoscope in a third embodiment; and FIG. 8B is an exploded sectional view after mounting taken along line VIIIB-VIIIB of FIG. 8A for explaining the circuit board of the capsule endoscope in the third embodiment.

DETAILED DESCRIPTION OF THE PREFERRED EMBODIMENT(S)

First Embodiment

Figure 1:
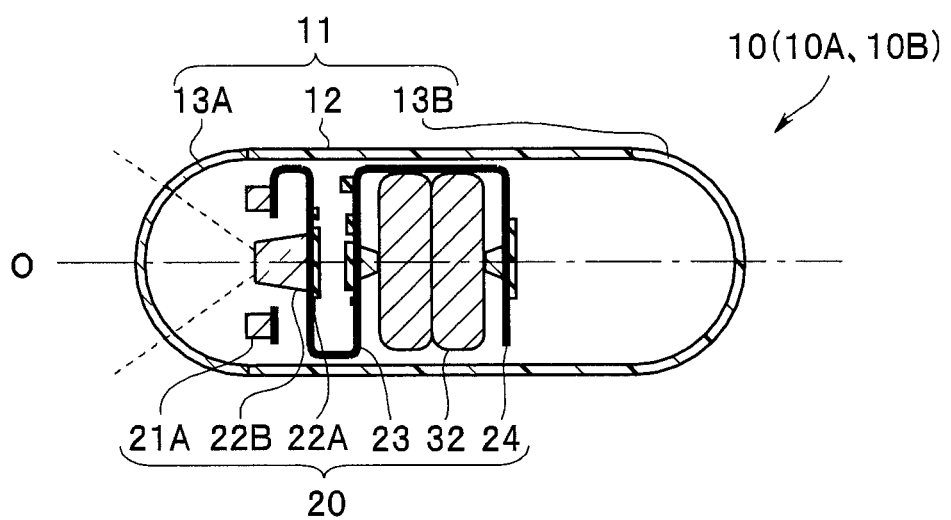
FIG. 1 is a sectional view of a capsule endoscope in a first embodiment.

As shown in FIG. 1, in a capsule endoscope (hereinafter referred to as "endoscope") 10, which is a capsule type medical device in the present embodiment, a circuit board 20 including various functional sections is housed inside a capsule type housing 11 in a bent state together with a battery 32.

The housing 11 includes a cylindrical main body section 12 and substantially semispherical end cover sections 13A and 13B at both ends of the main body section 12. The end cover section 13A is made of a transparent material. The main body section 12 and the end cover section 13B are made of an opaque material. However, the end cover section 13A and the main body section 12 and the end cover section 13B may be integrally molded. The elongated housing 11 has a rotationally symmetrical shape having a center axis O in a longitudinal direction as an axis of rotational symmetry. Length L of the housing 11, that is, length L in a direction of the center axis O is 25 to 35 mm. A diameter D in an orthogonal direction of the center axis O is 5 to 15 mm.

An image of an inside of a body illuminated by light emitting elements 21A arranged on the transparent end cover section 13A side is acquired by an image pickup chip 22A via a lens unit 22B. The battery 32, which is a power supply source, is disposed between a power supply board section 23 and a transmission board section 24, both of which have a substantially circular shape, of the circuit board 20 in a bent state.

Note that the circuit board 20 is housed in a housing together with a spacer member (not shown in the figure) for determining arrangement of the respective board sections.

Figure 2A:
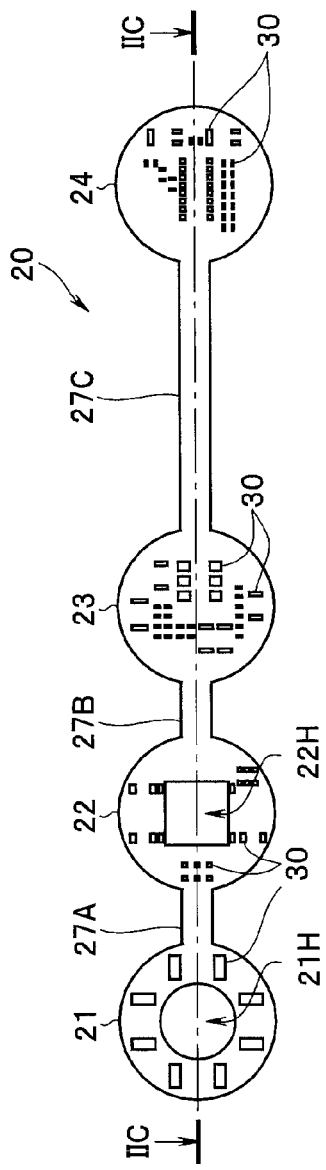
FIG. 2A is a top view for explaining a circuit board before mounting of the capsule endoscope in the first embodiment.
Figure 2B:
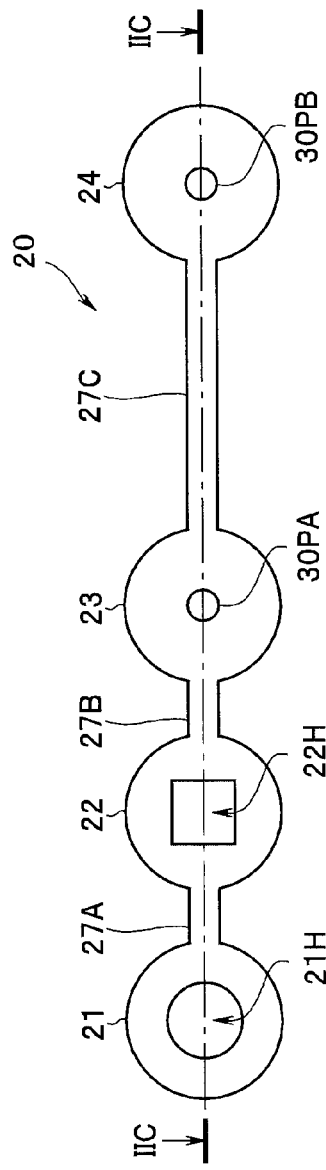
FIG. 2B is a bottom view for explaining the circuit board before mounting of the capsule endoscope in the first embodiment.
Figure 2C:
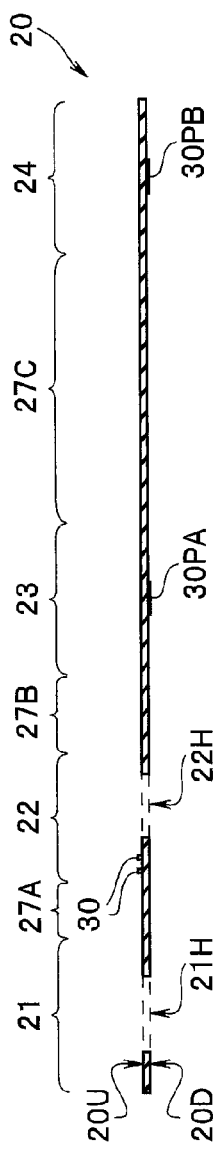
FIG. 2C is a sectional view taken along line IIC-IIC of FIG. 2A and FIG. 2B for explaining the circuit board before mounting of the capsule endoscope in the first embodiment.

As shown in FIG. 2A, FIG. 2B, and FIG. 2C, the circuit board 20 having flexibility, on which a plurality of substantially circular board sections are arranged in a row via connecting sections, is housed in the housing in a state in which the connecting sections are bent at 180 degrees (90 degrees+90 degrees) and principal planes of the respective board sections are orthogonal to the center axis O. FIG. 2A is a top view observed from a first principal plane 20U side, which is a mounting surface of the circuit board 20 before mounting. FIG. 2B is a bottom view observed from a second principal plane 20D side of the circuit board 20 before mounting. FIG. 2C is a sectional view taken along line IIC-IIC of FIG. 2A and FIG. 2B.

The circuit board 20 is an integral flexible wiring board having flexibility configured by arranging, in order, a first lighting board section 21, a connecting section 27A, a first image pickup board section 22, a connecting section 27B, the power supply board section 23, a connecting section 27C, and the transmission board section 24 in a row. Note that, in the following explanation, each of the connecting sections 27A, 27B, and 27C is referred to as connecting section 27.

On the first principal plane 20U of the circuit board 20, a plurality of connection electrodes 30 for mounting electronic components are formed. The connection electrodes 30 are, for example, made of a conductive material such as copper or gold. On the other hand, a connection electrode for electronic component mounting is not formed on the second principal plane 20D. In other words, an electronic component requiring electrical connection is not mounted on the second principal plane 20D. In bent parts of the connecting section 27, electronic components are not mounted on both the principal planes.

Mounting of various electronic components and the like on the first principal plane 20U of the circuit board 20 is performed by an SMT (surface mount technology) process.

Note that, on the second principal plane 20D, a wiring layer (not shown in the figure) formed by a plurality of wires connected to the electronic components mounted on the first principal plane 20U via a through-wire piercing through the circuit board 20 is formed. Openings 21H, 22H, and 23H are provided in the respective board sections 21 to 23 of the circuit board 20.

Next, the circuit board 20 having the electronic components and the like mounted thereon is explained using FIG. 3A and FIG. 3B. FIG. 3A is a top view observed from the first principal plane 20U side of the circuit board 20 having the electronic components and the like mounted thereon. FIG. 3B is an exploded sectional view taken along line IIIB-IIIB of FIG. 3A.

On the first principal plane 20U of the substantially circular first lighting board section 21, four light emitting elements 21A, for example, LEDs are mounted on the connection electrodes 30 around the substantially circular opening 21H. Note that the light emitting elements 21A are not limited to the LEDs. The number of the light emitting elements 21A is not limited to four.

The image pickup chip 22A is flip-chip mounted on the first principal plane 20U of the substantially circular first image pickup board section 22 in a state in which an image pickup surface is directed to a side of the substantially rectangular opening 22H. The lens unit 22B is arranged on the image pickup surface. As the image pickup chip 22A, a CCD or a CMOS image sensor or the like is used.

On the first principal plane 20U of the substantially circular power supply board section 23, chip components such as a power supply control IC (23A), an EEPROM (23B), a resistor (23C), a capacitor (23D), a diode (23E), and an inductor (23F) are surface-mounted. A land (electrode) for contact spring 30PA for battery connection is formed on the second principal plane 20D.

On the first principal plane 20U of the substantially circular transmission board section 24, a transmission IC (24A) configured to control a radio transmission signal and other chip components (24B to 24F) are mounted. A land for contact spring 30PB for battery connection is formed on the second principal plane 20D. Although not shown in the figure, a coil pattern, which is a transmission antenna, is also formed on the transmission board section 24.

Contact members 34A and 34B for battery connection are respectively connected to the lands for contact spring 30PA and 30PB for battery connection. The contact members 34A and 34B are preferably members including spring structures having elasticity.

Lands for contact spring 30PA and 30PB are, for example, made of a conductive material such as copper or gold. The lands for contact spring 30PA and 30PB are similar to the connection electrodes 30 for electronic component mounting. However, since the contact members 34A and 34B are metal wires having a simple spiral spring shape and are not electronic components, it is easy to connect the contact members 34A and 34B to the lands for contact spring 30PA and 30PB.

Note that not-shown various electronic components are also mounted on the first principal plane 20U of the circuit board 20. A plurality of wires are formed in the connecting sections 27, 24, and 26.

The opening 21H in a center of the first lighting board section 21 located at an end of the circuit board 20, which is an integral long flexible board, is bent to cover a frame of a lens unit 22B. Therefore, an assembly process for the circuit board 20 is possible by bending the circuit board 20 in order along the longitudinal direction and is easy because complicated bending work is unnecessary.

Note that members such as an image pickup lens (a lens unit) and the battery 32 are disposed on the principal plane 20D of the circuit board 20. Unlike the mounting of the electronic components and the like, it is easy to dispose the members such as the image pickup lens on the principal plane 20D. Therefore, productivity is not deteriorated.

That is, time required for mounting of the electronic components on both the surfaces (a first surface and a second surface) of the wiring board increases and productivity is deteriorated. In particular, the electronic components need to be mounted on the flexible circuit board having flexibility in a state in which the flexible wiring board is provisionally fixed to an adhesive conveying jig. When an SMT process on the first surface is completed, the wiring board is peeled off the adhesive conveying jig and an SMT process on the second surface is performed. However, the flexible wiring board sometimes curls when being peeled off the jig. Then, a yield of the SMT process on the second surface is sometimes lowered.

In the endoscope 10, the circuit board 20 is the flexible wiring board having flexibility. However, the electronic components are mounted only on the upper surface (the first surface) 20U. Therefore, it is possible to mount all the electronic components in a first SMT process. Therefore, it is possible to reduce time of a mounting process compared with implementation of the SMT processes on the respective both surfaces, that is, two times of the SMT processes. It is unlikely that a process yield is lowered.

As explained above, in the endoscope 10, since the circuit board 20 is a single-sided mounting wiring board, productivity is high.

Second Embodiment

Figure 4:
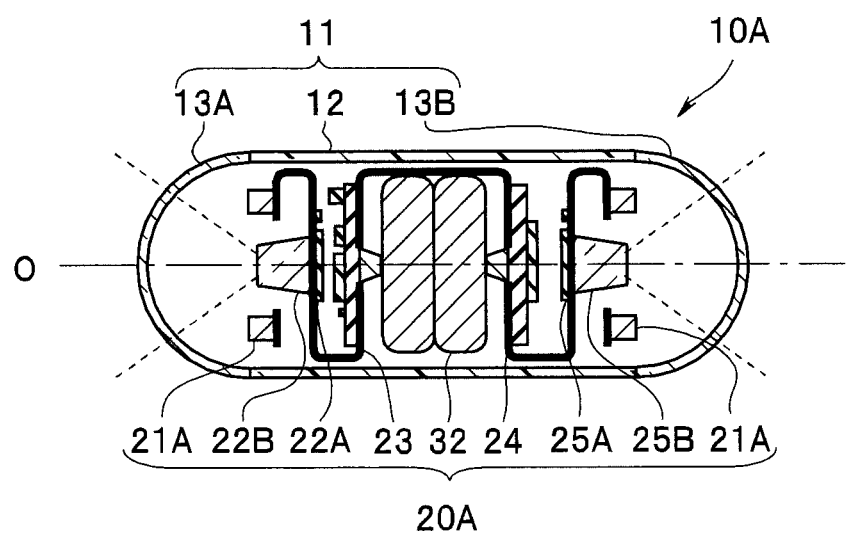
FIG. 4 is a sectional view of a capsule endoscope in a second embodiment.

As shown in FIG. 4, an endoscope 10A in a second embodiment is a so-called binocular type including two image pickup chips 22A and 25A configured to photograph visual fields in directions opposite to each other. Since the endoscope 10A is similar to the endoscope 10, the same components are denoted by the same reference numerals and signs and explanation of the components is omitted.

As shown in FIG. 5A to FIG. 6B, a circuit board 20A of the endoscope 10A is configured by arranging, in order, the first lighting board section 21, the connecting section 27A, the first image pickup board section 22, the connecting section 27B, the power supply board section 23, the connecting section 27C, the transmission board section 24, a connecting section 27D, a second image pickup board section 25, a connecting section 27E, and a second lighting board section 26 in a row.

The first lighting board section 21 and the second lighting board section 26 have substantially the same configuration. The first image pickup board section 22 and the second image pickup board section 25 also have substantially the same configuration.

In the endoscope 10A, unlike the endoscope 10, the power supply board section 23 and the transmission board section 24 are respectively formed as modules using multilayer wiring boards.

That is, on the first principal plane 20U of the substantially circular power supply board section 23, a power supply module 23P having substantially the same shape and the same size as the power supply board section 23 is mounted. Chip components such as the power supply control IC (23A), the EEPROM (23B), the resistor (23C), the capacitor (23D), the diode (23E), and the inductor (23F) are surface-mounted on one surface of the power supply module 23P. A plurality of connection terminals 30A for mounting the power supply module 23P on the circuit board 20A and a convex contact member 32A for battery connection are formed on the other surface. As contact members 32A and 32B, members including spring structures having elasticity may be mounted on the circuit board 20A.

On the first principal plane 20U of the substantially circular transmission board section 24, a transmission module 24P having substantially the same shape and the same size as the transmission board section 24 is mounted. The transmission IC (24A) configured to control a radio transmission signal and the other chip components (24B to 24F) are mounted on one surface of the transmission module 24P. A plurality of connection terminals 30B for mounting the transmission module 24P on the circuit board 20A and the contact member 32B for battery connection are formed on the other surface. In an inner layer of a first multilayer wiring board forming the transmission module 24P, although not shown in the figure, a coil pattern, which is a transmission antenna, is formed. The power supply module 23P and the transmission module 24P are also mounted on the first principal plane 20U of the circuit board 20A by an SMT process simultaneously with the other electronic components.

Unlike the circuit board 20, the power supply module 23P and the transmission module 24P are rigid wiring boards not having flexibility. Note that the power supply module 23P and the transmission module 24P may be wiring boards incorporated in electronic components.

That is, the endoscope 10A of the binocular type has a more complicated circuit configuration than the endoscope 10A of a monocular type. However, in the endoscope 10A, a power supply function and a transmission function are respectively formed as modules using multilayer wiring boards, whereby use of a single-sided wiring board having electronic components mounted only on the first principal plane 20U as the circuit board 20A is realized.

That is, since the flexible wiring board has its limitations of mounting density, when a large number of chip components and the like are directly mounted on the circuit board 20A, it is not easy to house the circuit board 20A inside the small housing 11. There is also a method of using a so-called rigid flexible board partially formed by a multilayer wiring board in order to increase the mounting density. However, costs substantially increase. On the other hand, in the endoscope 10A, the mounting density is partially improved by mounting the module components (the power supply module 23P and the transmission module 24P) formed by the multilayer wiring boards on the circuit board 20A, which is an inexpensive flexible wiring board. Further, a reduction in costs is realized compared with the use of the rigid flexible board.

Note that lighting modules having light emitting elements and electronic components mounted thereon and formed by substantially circular multilayer wiring boards may be mounted on the first lighting board section 21 and the second lighting board section 25. Further, image pickup modules having image pickup chips, lens units, and electronic components mounted thereon and formed by substantially circular multilayer wiring boards may be mounted on the first image pickup board section 22 and the second image pickup board section 26.

In the endoscope 10A, on mounting surfaces of the power supply module 23P and the transmission module 24P, the contact members 32A and 32B that project from the second principal plane 20D via substantially circular opening sections 23H and 24H when mounted on the circuit board 20A are mounted. The contact members 32A and 32B preferably include spring structures having elasticity. The battery 32 configured to supply electric power is disposed between the power supply board section 23 and the transmission board section 24. The power supply board section 23 and the transmission board section 24 having the multilayer wiring board mounted thereon are harder than the other portions of the circuit board 20A having flexibility. Since the battery 32 is sandwiched between the two hard board sections, it is easy to dispose the battery 32.

Since the battery 32 is held between the contact members 32A and 32B mounted on the power supply module 23P and the transmission module 24P, which are the rigid boards, it is easy to dispose the battery 32.

The two image pickup chips 22A and 25A of the endoscope 10A of the binocular type are disposed such that image pickup directions are set in opposite directions along the center axis O of the housing 11. In the endoscope 10A, the image pickup chips 22A and 25A are flip-chip mounted on the same first principal plane 20U of the first and second image pickup board sections 22 and 25. However, the image pickup directions are set in opposite directions by bending the connecting section 27. Note that, after the mounting process, image inspections of the image pickup chips 22A and 25A are performed before the circuit board 20A is bent. However, since light receiving surfaces of the two image pickup chips 22A and 25A face the same direction, it is possible to simultaneously perform the inspections and it is possible reduce an inspection time.

The two image pickup chips 22A and 25A are mounted to be rotationally symmetrical 180° on the circuit board 20A. Therefore, it is possible to reduce a design period by standardizing wiring layouts of the two image pickup board sections 22 and 25. Note that, when the image pickup chips 22A and 25A are mounted such that up and own directions of images picked up by the image pickup chips 22A and 25A face a direction perpendicular to a center axis direction of the circuit board 20A, in a bent state of the circuit board 20A, up and down directions of the two image pickup chips 22A and 25A are in directions opposite to each other with respect to the center axis direction. However, if the images are read out oppositely upward and downward during readout processing for the images, it is possible to display the images with the up and down directions aligned.

Lens units 22B and 25B are formed by housing plastic lenses in lens frames made of resin. The lens units 22B and 25B are aligned with respect to the image pickup chips 22A and 25A and bonded and fixed on a surface (the second principal plane 20D) on an opposite side of a mounting surface (the first principal plane 20U) of the circuit board 20A. Insides of the lens frames are hermetically sealed by thermosetting resin. To prevent air in a sealed space from being expanded by heat during hardening to cause a crack or the like, it is necessary to form ventilation passages during application of the resin and close the ventilation passages with the resin after the hardening. Directions in which the ventilation passages of the two lens frames, that is, the image pickup chips 22A and 25A are formed are aligned. Consequently, since it is unnecessary to change an application method between the two lens frames, it is possible to simplify a process of the sealing resin application.

The endoscope 10A in the present embodiment has the same effect as the endoscope 10. Further, although the endoscope 10A is the binocular type, it is possible to make a manufacturing process efficient.

Note that, as shown in FIG. 7, it is preferable that the circuit board 20A be manufactured in a state of an aggregate board including a plurality of circuit boards 20A1 to 20An (n is an integer) and a mounting process for electronic components is performed on an aggregate board 20X. As both of a mounting process for the image pickup chips 22A and 25A and a mounting process for the lens frames, mounting is performed using resin. Mounting of the image pickup chips 22A and 25A is preferably performed in order of the first image pickup chip 22A and the second image pickup chip 25A of the first circuit board 20A1, the first image pickup chip 22A and the second image pickup chip 25A of the second circuit board 20A2, and so on. Even if a failure occurs in a resin application amount at a certain point in time, circuit boards mounted before the failure occurs are non-defective products. Therefore, it is possible to reduce the number of defective products.

Third Embodiment

As shown in FIG. 8A and FIG. 8B, an endoscope 10B in a third embodiment is similar to the endoscope 10 in the first embodiment. However, the power supply module 23P and the transmission module 24P are respectively formed as modules using multilayer wiring boards as in the endoscope 10A and mounted on a circuit board 20B.

Therefore, the endoscope 10B has the same effect as the endoscope 10 and the like.

Note that, in the above explanation, the monocular or binocular capsule endoscope is explained as an example. However, trinocular and stereoscopic capsule endoscopes have the same effect. Further, the capsule type medical device in the embodiments of the present invention is not limited to the capsule endoscope and can be applied to various capsule type medical instruments such as a capsule type medical instrument for digestive fluid sampling, a pH sensor of a swallow type, and a drug delivery system.

The present invention is not limited to the embodiments explained above and various alterations, modifications, and the like are possible in a range in which the gist of the present invention is not changed.

What is claimed is:

1. A capsule type medical device comprising:
   a capsule type housing; and
   a circuit board including a first principal side and a second principal side, the first and second principal sides being separated by a thickness of the circuit board in an unbent shape, the circuit board having a plurality of board sections in a row arranged thereon, wherein the circuit board is housed inside the capsule type housing in a bent state, the circuit board including:
   an electronic component having a mounting surface;
   a connection electrode for electrically mounting the mounting surface of the electronic component to the first principal side of the circuit board in a fixed manner, the connection electrode being formed only on the first principal side, and
   a contact member fixed to the mounting surface of the electronic component, the electronic component being disposed on the first principal side over an opening section in the circuit board such that the contact member extends from the mounting surface of the electronic component through the opening section and projects towards the second principal side via the opening section in the circuit board.

2. The capsule type medical device according to claim 1, wherein the circuit board includes:
   a lighting board section having a plurality of light emitting elements mounted thereon;
   an image pickup board section having an image pickup chip configured to acquire image data mounted thereon;
   a transmission board section having a transmission module formed by a first multilayer wiring board and configured to transmit the image data by radio mounted thereon; and
   a power supply board section having a power supply module formed by a second multilayer wiring board and configured to control power supply mounted thereon.

3. The capsule type medical device according to claim 2, wherein the contact member comprises first and second contact members, the capsule type medical device further comprising a battery disposed between the first contact member arranged on the power supply module to project towards the second principal side towards one terminal of the battery and the second contact member arranged on the transmission module to project towards the second principal side towards another terminal of the battery.

4. The capsule type medical device according to claim 3, wherein:
   the lighting board section comprises a first lighting board section and a second lighting board section respectively arranged at both ends of a main body section of the capsule type housing, the first and second lighting board sections being configured to direct light in opposite directions; and the image pickup board section comprises a first image pickup board section and a second image pickup board section configured to pick up images in the opposite directions.

5. The capsule type medical device according to claim 3, wherein at least one of the first and second contact members has a spring structure.

6. The capsule type medical device according to claim 1, wherein the contact member has a height greater than the thickness of the circuit board so as to project from the second principal side, the thickness being a dimension between the first and second principal sides.

7. The capsule type medical device according to claim 1, wherein the contact member having a contact surface for contacting a surface of an electrical component in a non-fixed manner.

8. The capsule type medical device according to claim 7, wherein the electrical component is a battery.

9. The capsule type medical device according to claim 7, wherein the contact member does not contact any portions of the circuit board.

10. The capsule type medical device according to claim 1, wherein the electronic component is a non-battery electronic component.

* * * * *